United States Patent [19]

Nakayama et al.

[11] Patent Number: 4,548,899
[45] Date of Patent: Oct. 22, 1985

[54] SILVER HALIDE COLOR PHOTOGRAPHIC MATERIAL

[75] Inventors: Noritaka Nakayama; Satoshi Kawakatsu; Katsunori Katoh, all of Hachioji; Kaoru Shinozaki, Tokyo, all of Japan

[73] Assignee: Konishiroku Photo Industry Co., Ltd., Tokyo, Japan

[21] Appl. No.: 667,465

[22] Filed: Nov. 1, 1984

[30] Foreign Application Priority Data

Nov. 2, 1983 [JP] Japan .................. 58-206321
Nov. 15, 1983 [JP] Japan .................. 58-214853

[51] Int. Cl.⁴ ............................. G03C 7/26
[52] U.S. Cl. .................. 430/558; 430/386; 430/387
[58] Field of Search .................. 430/558, 386, 387

[56] References Cited

U.S. PATENT DOCUMENTS

| | | | |
|---|---|---|---|
| 3,725,067 | 4/1973 | Bailey et al. | 430/558 |
| 4,338,393 | 7/1982 | Bailey et al. | 430/558 |
| 4,401,752 | 8/1983 | Lau | 430/385 |
| 4,443,536 | 4/1984 | Lestina | 430/558 |
| 4,500,630 | 2/1985 | Sato et al. | 430/386 |
| 4,503,141 | 3/1985 | Furutachi et al. | 430/558 |

Primary Examiner—J. Travis Brown
Attorney, Agent, or Firm—Finnegan, Henderson, Farabow, Garrett & Dunner

[57] ABSTRACT

A silver halide color photographic material is disclosed which has at least one silver halide emulsion layer on a support, said silver halide emulsion layer containing at least one magenta coupler of the following formula (I) or (II):

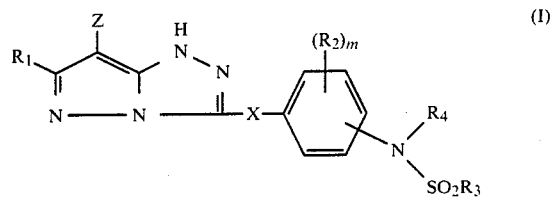

(I)

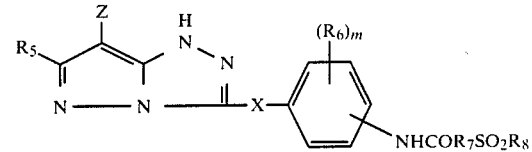

(II)

wherein $R_1$ and $R_4$ are each a hydrogen atom, an alkyl group or an aryl group; $R_2$ and $R_6$ are each a monovalent group; $R_3$ is an alkyl group, an aryl group or a heterocyclic group; $R_5$ is an alkyl group or an aryl group; $R_7$ is an alkylene group, an arylene group or a bivalent organic group having at least one alkylene bonded to at least one arylene; $R_8$ is an alkyl group, an alkenyl group, an aryl group or a heterocyclic group; X is a single bond or an alkylene group having 1 to 5 carbon atoms; Z is a hydrogen atom or a group that can be eliminated upon coupling reaction with the oxidized product of a color developing agent; and m is an integer of 0 to 4.

17 Claims, No Drawings

SILVER HALIDE COLOR PHOTOGRAPHIC MATERIAL

FIELD OF THE INVENTION

The present invention relates to a silver halide color photographic material which provides a magenta dye image having high sensitivity, color density and improved keeping quality.

In silver halide color photography, silver halide grains that have been exposed to light are reduced by an aromatic primary amine color developing agent, and the resulting oxidized product of the developing agent couples with a yellow, magenta or cyan dye forming coupler to form a respective dye image.

Pyrazolone couplers are commonly used as the magenta dye forming coupler, but they have low maximum color density and sensitivity, and absorptions other than the predominant one which are undesired. Furthermore, these couplers do not have sufficient long-term stability, and in particular, they are low in resistance to formalin and experience appreciable change in color and decrease in color formability.

In order to eliminate these defects, several proposals have been made. Japanese Patent Publication No. 30895/1973 shows a 1H-pyrazolo(3,2-c)-s-triazole magenta coupler having no undesired absorption other than the predominant one. However, with this coupler, little improvement has been achieved with respect to maximum color density, sensitivity and resistance to formalin.

Japanese Patent Publication No. 16058/1974 shows a bis-pyrazolone magenta coupler. This coupler has some improvement in sensitivity and formalin resistance, but not in maximum color density.

Japanese Patent Public Disclosure No. 42045/1983 shows the use of a coupler ballast group having a terminal hydroxyphenylene sulfonyl group for the purpose of providing an improved maximum color density. However, the obtained maximum color density is not as high as desired.

SUMMARY OF THE INVENTION

One object of the present invention is to provide a photographic magenta coupler which has high maximum color density, high sensitivity and improved resistance to formalin.

Another object of the present invention is to provide a photographic magenta coupler which does not have any absorption other than the principal absorption that is undesired.

A further object of the present invention is to provide a photographic magenta coupler having improved dispersion stability.

A still further object of the present invention is to provide a silver halide color photographic material which affords a color image of good quality by using a photographic magenta coupler having the desired characteristics shown above.

These objects of the present invention can be achieved by a silver halide color photographic material having at least one silver halide emulsion layer on a support, said silver halide emulsion layer containing at least one magenta coupler of formula (I) or (II) given below:

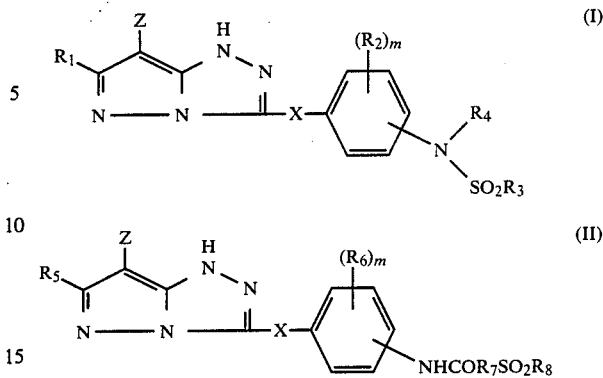

wherein $R_1$ and $R_4$ are each a hydrogen atom, an alkyl group or an aryl group; $R_2$ and $R_6$ are each a monovalent group; $R_3$ is an alkyl group, an aryl group or a heterocyclic group; $R_5$ is an alkyl group or an aryl group; $R_7$ is an alkylene group, an arylene group or a bivalent organic group having at least one alkylene bonded to at least one arylene; $R_8$ is an alkyl group, an alkenyl group, an aryl group or a heterocyclic group; X is a single bond or an alkylene group having 1 to 5 carbon atoms; Z is a hydrogen atom or a group that can be eliminated upon coupling reaction with the oxidized product of a color developing agent; and m is an integer of 0 to 4.

DETAILED DESCRIPTION OF THE INVENTION

As shown above, $R_1$ in formula (I) represents a hydrogen atom, an alkyl group or an aryl group, and in formula (II), $R_5$ represents an alkyl group or an aryl group. Preferred alkyl groups are those having 1 to 8 carbon atoms. More preferred alkyls are those having 1 to 4 carbon atoms, such as methyl, ethyl, ethoxyethyl and t-butyl.

A preferred aryl group represented by $R_1$ or $R_5$ is a phenyl group which may be substituted as in p-methoxyphenyl, m-chlorophenyl or p-(t)-butylphenyl.

The symbols $R_2$ and $R_6$ each represent a monovalent group such as a halogen atom (e.g. chlorine), an alkoxy group (e.g. methoxy or t-butoxy), an alkyl group (e.g. methyl, ethyl, methoxyethyl or benzyl), a nitro group, or a cyano group.

The symbol $R_3$ represents an alkyl group, an aryl group or a heterocyclic group, with alkyl and aryl groups being preferred. Preferred alkyl groups are those having 1 to 25 carbon atoms, such as straight- or branched-chain alkyl groups (e.g. methyl, isopropyl, t-butyl and dodecyl). These alkyl groups may have substituents, and preferred substituents are a halogen atom, a nitro group, a cyano group, an aryl group, an alkoxy group, an aryloxy group, a carboxy group, an alkylthio group, an arylthio group, a carbonyl group, a sulfamoyl group, an acylamino group, a sulfonyl group, a sulfinyl group, a hydroxy group and a heterocyclic group.

The aryl group as a substituent on the alkyl group ($R_3$) and the aryl group as $R_3$ are preferably a phenyl group which may have a substituent. Preferred substituents include a halogen atom, an alkyl group, a nitro group, a cyano group, an alkoxy group, an aryloxy group, a carboxy group, a sulfamoyl group, a carbamoyl group, an acylamino group, a dialkylamino group, a sulfonyl group, a sulfinyl group, and a hydroxyl group.

The symbol $R_4$ in formula (I) represents a hydrogen atom, an alkyl group or an aryl group, with the hydrogen atom and alkyl group being preferred. Alkyl groups having 1 to 38 carbon atoms are preferred, and those having 1 to 4 carbon atoms are particularly preferred, such as methyl, ethyl, ethoxyethyl and t-butyl groups. These alkyl groups may optionally be substituted.

The aryl group as $R_4$ is preferably a phenyl group which may have a substituent. Illustrative substituted phenyl groups are p-methoxyphenyl, m-chlorophenyl and p-(t)-butylphenyl groups.

The symbols $R_7$ in formula (II) represents an alkylene group, an arylene group or a bivalent organic group having at least one alkylene bonded to at least one arylene. An alkylene group is preferred. Preferred alkylene groups are those having 1 to 20 carbon atoms, such as methylene, 1,1-ethylene, 1,3-propylene, 1,1-dodecylene, 1,1-tridecylene and 1-methyl-2-ethylene.

The arylene group as $R_7$ is preferably a phenylene group which may have a substituent. Illustrative substituted phenylene groups are 4methyl-o-phenylene, 3-chloro-m-phenylene and 3-methoxy-p-phenylene.

The other definition for $R_7$ is a divalent organic group having at least one alkylene bonded to at least one arylene, and illustrative examples are an alkylene-arylene group, an arylene-alkylene group, an alkylene-arylene-alkylene group, and an arylene-alkylene-arylene group. The alkylene and/or arylene in these groups may be substituted. Specific examples of the divalent organic group having at least one alkylene bonded to at least one arylene are given below:

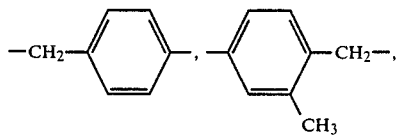

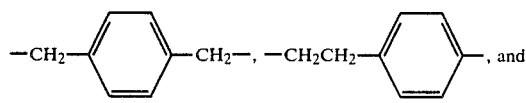

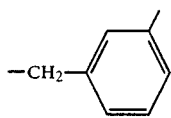

The symbol $R_8$ in formula (II) represents an alkyl group, an alkenyl group, an aryl group or a heterocyclic group, with alkyl and aryl groups being preferred. Preferred alkyl groups are those having 1 to 20 carbon atoms, such as methyl, ethyl, iso-propyl, n-butyl, n-hexyl, cyclohexyl, n-nonyl, n-dodecyl, n-octadecyl, benzyl and phenetyl groups.

A preferred aryl group is phenyl which may have a substituent such as a halogen atom, an alkyl group, an alkoxy group, a carboxy group, an alkylamino group, a sulfonamido group or an alkyloxycarbonyl group. Illustrative substituted phenyl groups include m-chlorophenyl, p-carboxyphenyl, p-dimethylaminosulfonamidophenyl, p-toluyl, 3,5-dimethylphenyl, p-tert-butylphenyl, p-n-dodecylphenyl, p-methoxyphenyl, p-tert-butoxyphenyl, p-n-dodecyloxyphenyl, p-n-tetradecyloxyphenyl, 2-tert-butyl-5-dodecylphenyl, 2-n-butyloxy-5-tert-octylphenyl, m-dodecyloxycarbonylphenyl and o-ethoxycarbonylphenyl groups.

Examples of the alkenyl group represented by $R_8$ are propenyl and butenyl.

Examples of the heterocyclic group as $R_8$ include thiazole, thiadiazole, benzoxazole and tetrazole which may have substituents. Illustrative substituted heterocyclic groups include thiazole-2-yl, 5-methylthiadiazole-2-yl, benzoxazole-2-yl and 1-methyltetrazole-5-yl.

The group represented by Z which can be eliminated upon coupling reaction with the oxidized product of a color developing agent means a "split-off" group present in conventional two-equivalent couplers, and does not include a hydrogen atom. Specific examples of this split-off group include a halogen atom (e.g. chlorine or fluorine), an aryloxy group (e.g. phenoxy, p-methoxyphenoxy, p-butane-sulfonamidophenoxy, or p-tert-butylcarboamidophenoxy), an arylthio group (e.g. phenylthio) and a heterocyclic thio group (e.g. 1-ethyltetrazole-5-thioyl). A halogen atom is preferred, and a chlorine atom is particularly preferred.

Examples of X represented by formulas (I) and (II) are such as methylene, 1,1-ethene, 1,2-ethylene, 1,3-propylene, 1,1-propylene, 1,2-propylene, 1,4-buthylene and 1,5-penthylene. Preferably X is represented by $-(CH_2)_l-$ (wherein l is an integer of 0 to 5, preferably 1 to 3).

The symbol m in formulas (I) and (II) represents an integer of 0 to 4. In a particularly preferred case wherein m is 0, both the group

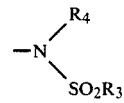

in formula (I) and the group $-NHCOR_7SO_2R_8$ in formula (II) are preferably ballast groups sufficient to render non-diffusible the photographic magenta couplers of each formula.

The groups

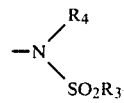

and $-NHCOR_7SO_2R_8$ may be bonded to the phenyl group at any position with respect to the position where the group

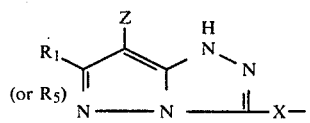

is bonded to the phenyl group. Bonding at a para-position is particularly preferred.

When $R_7$ is an alkylene group, $R_8$ may be an alkyl group, an alkenyl group, an aryl group or a heterocyclic group, provided that the total number of carbon atoms including those present in a possible substituent preferably ranges from 8 to 30, more preferably from 12 to 25. If $R_7$ is a phenylene group, $R_8$ is preferably an alkyl group or phenyl group. The phenyl group as $R_8$ may be substituted, and a preferred substituent is selected from among alkyl, alkoxy and alkoxycarbonyl groups. The alkyl group as $R_8$ or the alkyl group, alkoxy group or alkoxycarbonyl group as a substituent on the phenyl group preferably has 8 to 30 carbon atoms, with the range of 8 to 20 being particularly preferred.

Typical examples of the magenta couplers represented by formulas (I) and (II) are listed below, but it should be understood that the scope of the present invention is by no means limited to these examples.

| Coupler No. | $R_1$ | Z | X | | $R_3$ | Formula (I) |
|---|---|---|---|---|---|---|
| M-1 | $CH_3-$ | Cl— | $\text{-(CH}_2\text{)}_3\text{-}$ | 4-NHSO$_2$- phenyl | 4-OC$_{12}$H$_{25}$-phenyl | |
| M-2 | $CH_3-$ | H— | $\text{-(CH}_2\text{)}_3\text{-}$ | 4-NHSO$_2$- phenyl | 2-(CH$_2$)$_3$O-, 5-C$_5$H$_{11}$(t), with C$_5$H$_{11}$(t) phenyl | |
| M-3 | $CH_3-$ | H— | $-CH_2-$ | 2-NHSO$_2$- phenyl | 4-CH$_3$-phenyl | |
| M-4 | $CH_3-$ | H— | $\text{-(CH}_2\text{)}_3\text{-}$ | 4-(N-C$_{12}$H$_{25}$)(SO$_2$-)-phenyl | -C$_4$H$_9$(n) | |
| M-5 | $CH_3-$ | 4-CH$_3$-phenoxy | $\text{-(CH}_2\text{)}_3\text{-}$ | 3-Cl, 5-NHSO$_2$- phenyl | 4-(4-C$_{12}$H$_{25}$-phenoxymethyl)phenyl | |
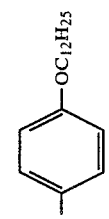

| Coupler No. | $R_1$ | Z | Formula (I) | X | | $R_3$ |
|---|---|---|---|---|---|---|
| M-6 | $C_2H_5-$ | Cl- | | $-(CH_2)_3-$ | 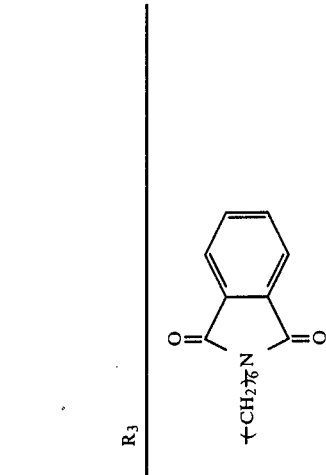 | 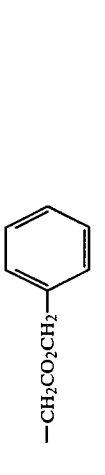 |
| M-7 | $CH_3-$ | H- | | $-(CH_2)_3-$ |  | $-CH_2CO_2CH_2-$ |
| M-8 |  | Cl- | | $-(CH_2)_2-$ |  |  |
| M-9 | H- |  | | $-(CH_2)_3-$ |  | $-(CH_2)_2NHC_{14}H_{29}(n)$ |

-continued

Formula (I)

[Structure of Formula (I): pyrazolo-triazole core with R₁, Z substituents, and linker –X– to phenyl ring with (R₂)ₘ substituents and N(R₄)–SO₂R₃ group]

| Coupler No. | $R_1$ | Z | $R_4$ / (R₂)ₘ-phenyl-N(R₄)SO₂– | X | $R_3$ |
|---|---|---|---|---|---|
| M-10 | $CH_3-$ | $Br-$ | 4-($C_2H_5$)-phenyl-NHSO₂– | $-(CH_2)_2-$ | $-(CH_2)_2-N(C_3H_7(n))-CH_2-C_6H_5$ |
| M-11 | $(CH_3)_3C-$ | $C_6H_5-S-$ | 2-$OCH_3$, 5-methyl-phenyl-NHSO₂– | $-(CH_2)_2-$ | cyclohexyl (H position shown) |
| M-12 | $C_6H_5-$ | [1,2,4-triazole-3-thio with H-N, $C_2H_5$-N] | 4-methyl-phenyl-NHSO₂– | $-(CH_2)_2-$ | $-CH_2CH_2SO_2C_{12}H_{25}(n)$ |
| M-13 | $CH_3-$ | $Cl-$ | 4-methyl-phenyl-NHSO₂– | $-(CH_2)_3-$ | 4-($NHCOC_{11}H_{23}$)-phenyl |
| M-14 | $CH_3-$ | $Cl-$ | 4-methyl-phenyl-NHSO₂– | $-(CH_2)_3-$ | $-(CH_2)_2-O-C(=O)-C_{13}H_{27}(n)$ |

-continued

Formula (I)

$$\text{structure: pyrazolo ring with } R_1, Z, \text{ and } N=N-\overset{H}{N}-\underset{N}{\overset{}{=}}-X-\text{phenyl}(R_2)_m-N(R_4)-SO_2R_3$$

Second structure variant: phenyl$(R_2)_m$–N(R_4)–SO_2–

| Coupler No. | $R_1$ | Z | X | (aryl group) | $R_3$ |
|---|---|---|---|---|---|
| M-15 | $C_5H_{11}-$ | Cl— | $+CH_2+_3$ | 4-NHSO$_2$– phenyl (with 3-CH$_3$) | $+CH_2+_3OC(CH_2)_4COC_2H_5$ (with two =O) |
| M-16 | $CH_3-$ | Cl— | $+CH_2+_3$ | 3-Cl, 5-CH$_3$ phenyl-NHSO$_2$– | $-CH(C_{16}H_{33}(n))-CO_2C_2H_5$ |
| M-17 | $C_3H_7-$ | Cl— | $+CH_2+_3$ | 3-CH$_3$ phenyl-N(C$_{10}$H$_{21}$)-SO$_2$– | $-CH_2-CO_2H$ |
| M-18 | $CH_3-$ | Cl— | $+CH_2+_2$ | 2-C$_2$H$_5$, phenyl-NHSO$_2$– | $-CH_2CH_2NCOCH_2O-$ phenyl-$OC_8H_{17}(t)$ (N-cyclohexyl, H) |
| M-19 | H— | Cl— | $+CH_2+_2$ | 3-CH$_3$ phenyl-NHSO$_2$– | $-CH(C_6H_5)-CO_2C_{14}H_{29}(n)$ |

-continued

Formula (I)

| Coupler No. | $R_1$ | Z | X | (structure with $(R_2)_m$, $R_4$, $SO_2R_3$) | $R_3$ |
|---|---|---|---|---|---|
| M-20 | $CH_3-$ | $Cl-$ | $-(CH_2)_2-$ | 4-methylphenyl-NHSO$_2-$ | $-CH(C_6H_5)-CN$ |
| M-21 | $CH_3-$ | $Cl-$ | $-(CH_2)_2-$ | 3-Cl-5-methylphenyl-NHSO$_2-$ | $-C(CO_2CH_3)(CH_3)-CH_2SC_{12}H_{25}(n)$ |
| M-22 | $CH_3-$ | $Cl-$ | $-(CH_2)_3-$ | 4-methylphenyl-NHSO$_2-$ | 2,4-bis($C_5H_{10}OH$)phenyl-O-$(CH_2)_3-$ |
| M-23 | $CH_3-$ | $Cl-$ | $-(CH_2)_3-$ | 4-methylphenyl-NHSO$_2-$ | $-(CH_2)_2-Cl$ |
| M-24 | $CH_3-$ | $Cl-$ | $-(CH_2)_3-$ | 4-methylphenyl-N(CH$_2$-4-OC$_{12}$H$_{25}$-C$_6$H$_4$)-SO$_2-$ | $-C_8H_{17}$ |

-continued

Formula (I)

| Coupler No. | $R_1$ | Z | X | | $R_3$ |
|---|---|---|---|---|---|
| M-25 | (t)C$_4$H$_9$—⟨phenyl⟩— | Cl— | ⫶CH$_2$⫶ | —⟨phenyl⟩—NHSO$_2$— | —CH$_2$CN |
| M-26 | CH$_3$— | Cl— | ⫶CH$_2$⫶ | —⟨phenyl⟩—NHSO$_2$— | —CH$_2$CH$_2$N(CH$_3$)—SO$_2$—(tetrahydrothiophene SO$_2$) |
| M-27 | CH$_3$— | Cl— | ⫶CH$_2$⫶ | —⟨phenyl⟩—NHSO$_2$— | —CH(CO$_2$CH$_2$CH$_2$O—⟨phenyl⟩—C$_4$H$_9$(t))—CH(CO$_2$CH$_2$CH$_2$O—⟨phenyl⟩—C$_4$H$_9$(t)) |
| M-28 | CH$_3$— | Cl— | —CH$_2$— | —⟨phenyl⟩—NHSO$_2$— | —CH(CONHC$_8$H$_{17}$(n))CONHC$_8$H$_{17}$(n) |
| M-29 | CH$_3$— | Cl— | —CHCH$_2$—CH$_3$ | —⟨phenyl⟩—NHSO$_2$— | —⟨phenyl⟩—OC$_{12}$H$_{25}$(n) |

-continued
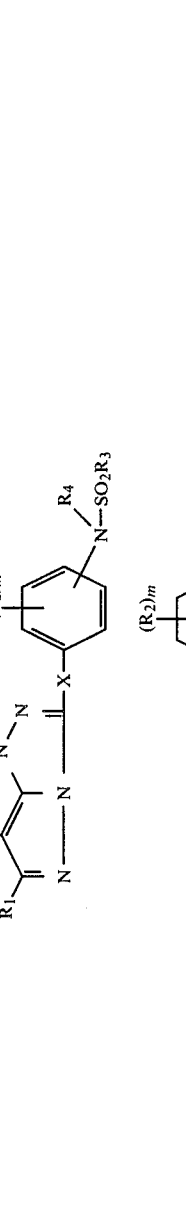
| Coupler No. | R₁ | Z | X | (R₂)ₘ | R₄ | R₃ | Formula (I) |
|---|---|---|---|---|---|---|---|
| M-30 | CH₃— | Cl— | $-\underset{C_2H_5}{\underset{|}{CH}}-$ | | NHSO₂— | 4-OC₄H₉, 4-C₈H₁₇(t) phenyl | |

Formula (II)

[Structure: pyrazole-hydrazone coupler with R5, Z substituents on pyrazole ring connected via NH-N=C-X to phenyl ring bearing (R6)m and NHCOR7SO2R8 groups]

| Coupler No. | $R_5$ | Z | X | (R6)m — NHCO— phenyl | —$R_7SO_2R_8$ |
|---|---|---|---|---|---|
| M - 31 | $CH_3-$ | $-Cl$ | $-(CH_2)_2-$ | —phenyl—NHCO— | $-\underset{\underset{C_2H_5}{\mid}}{C}HSO_2C_{12}H_{25}$ |
| M - 32 | $CH_3-$ | $-Cl$ | $-(CH_2)_3-$ | —phenyl—NHCO— | $-\underset{\underset{CH_3}{\mid}}{\overset{\overset{CH_3}{\mid}}{C}}-SO_2C_{18}H_{37}$ |
| M - 33 | $CH_3-$ | $-Cl$ | $-(CH_2)_3-$ | —phenyl—NHCO— | $-\underset{\underset{C_{12}H_{25}}{\mid}}{C}HSO_2CH_2-phenyl$ |
| M - 34 | phenyl- | $-O-$phenyl | $-CH_2-$ | —phenyl(o-NHCO—) | $-\underset{\underset{C_{12}H_{25}}{\mid}}{C}HSO_2-$phenyl$-Cl$ |
| M - 35 | $CH_3-$ | $-Cl$ | $-(CH_2)_3-$ | —phenyl—NHCO— | $-\underset{\underset{C_{12}H_{25}}{\mid}}{C}HSO_2-$phenyl$-C_4H_9(t)$ |
| M - 36 | $CH_3CH_2-$ | $-F$ | $-(CH_2)_2-$ | —phenyl—NHCO— | $-\underset{\underset{C_{10}H_{21}}{\mid}}{C}HSO_2CH=CH-$phenyl |
| M - 37 | $CH_3-$ | $-O-$phenyl$-OCH_3$ | $-(CH_2)_3-$ | —phenyl—NHCO— | $-\underset{\underset{C_3H_7(iso)}{\mid}}{C}HSO_2C_{12}H_{25}$ |
| M - 38 | $CH_3O-$phenyl- | $-Cl$ | $-(CH_2)_4-$ | phenyl (Cl, NHCO—) | $-\underset{\underset{C_{16}H_{33}}{\mid}}{C}HSO_2-$phenyl$-OCH_3$ |
| M - 39 | $CH_3-$ | $-Cl$ | $-(CH_2)_3-$ | —phenyl—NHCO— | $-\underset{\underset{C_2H_5}{\mid}}{C}HSO_2-$phenyl$-OC_{12}H_{25}$ |
| M - 40 | $CH_3CH_2-$ | $-Cl$ | $-(CH_2)_3-$ | —phenyl—NHCO— | $-\underset{\underset{CH_3}{\mid}}{C}HCH_2SO_2C_{12}H_{25}$ |
| M - 41 | $(t)C_4H_9-$ | $-Cl$ | $-(CH_2)_2-$ | —phenyl—NHCO— | $-\underset{\underset{C_{18}H_{37}}{\mid}}{C}HSO_2-$cyclohexyl |
| M - 42 | $CH_3-$ | 1-phenyl-tetrazol-5-ylthio (-S-tetrazole-N-phenyl) | $-(CH_2)_2-$ | —phenyl—NHCO— | $-\underset{\underset{C_{12}H_{25}}{\mid}}{C}HSO_2-$benzoxazol-2-yl |

-continued

Formula (II)

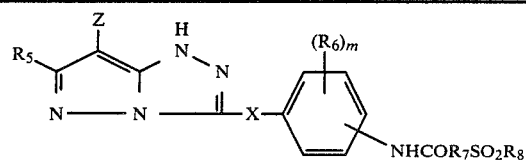

| Coupler No. | $R_5$ | Z | X | ⌬NHCO— | —$R_7SO_2R_8$ |
|---|---|---|---|---|---|
| M-43 | $CH_3$— | —Cl | $+CH_2\!\!\mathop{)}\limits_{3}$ | 3-CN, 5-NHCO-phenyl | —CH($C_{10}H_{21}$)SO$_2$CH$_2$CH$_2$—phenyl |
| M-44 | (t)$C_4H_9$— | —Cl | $+CH_2\!\!\mathop{)}\limits_{3}$ | —phenyl-NHCO— | —CH($C_{12}H_{25}$)SO$_2$—CH=CH—CH$_3$ |
| M-45 | $CH_3$— | —Cl | $+CH_2\!\!\mathop{)}\limits_{2}$ | —phenyl-NHCO— | —phenyl-SO$_2C_{12}H_{25}$ |
| M-46 | $CH_3$— | —Cl | $+CH_2\!\!\mathop{)}\limits_{3}$ | —phenyl-NHCO— | —phenyl-SO$_2$-phenyl-OC$_{12}H_{25}$ |
| M-47 | $CH_3$— | —Cl | —$CH_2$— | 2-CH$_3$-phenyl-NHCO— | 2-SO$_2C_{12}H_{25}$, 4-$C_4H_9$(t)-phenyl |
| M-48 | (t)$C_4H_9$— | —Cl | $+CH_2\!\!\mathop{)}\limits_{3}$ | —phenyl-NHCO— | —CH($C_{12}H_{25}$)SO$_2$—phenyl—COOCH$_3$ |
| M-49 | $CH_3$— | —Cl | $+CH_2\!\!\mathop{)}\limits_{3}$ | —phenyl-NHCO— | —CH($C_{12}H_{25}$)—SO$_2C_2H_5$ |
| M-50 | $CH_3$— | —Cl | $+CH_2\!\!\mathop{)}\limits_{3}$ | —phenyl-NHCO— | —CH($C_{10}H_{21}$)SO$_2$CH$_2$—phenyl—$C_4H_9$(t) |
| M-51 | $CH_3$— | —Cl | $+CH_2\!\!\mathop{)}\limits_{3}$ | —phenyl-NHCO— | —CH$_2$—phenyl—SO$_2C_{12}H_{25}$ |
| M-52 | $CH_3$— | —Cl | $+CH_2\!\!\mathop{)}\limits_{3}$ | —phenyl-NHCO— | —CH$_2$—phenyl—CH$_2$SO$_2C_{10}H_{21}$ |
| M-53 | (t)$C_4H_9$— | —Cl | $+CH_2\!\!\mathop{)}\limits_{3}$ | —phenyl-NHCO— | —phenyl—CH$_2$SO$_2C_{12}H_{25}$ |
| M-54 | $CH_3$— | —Cl | $+CH_2\!\!\mathop{)}\limits_{3}$ | —phenyl-NHCO— | 3-CH$_2$SO$_2C_8H_{17}$, 5-CH$_3$-phenyl |
| M-55 | $CH_3$— | —Cl | $+CH_2\!\!\mathop{)}\limits_{3}$ | —phenyl-NHCO— | —CH$_2$—CH$_2$—phenyl—SO$_2C_{12}H_{25}$ |
| M-56 | $CH_3$— | Cl— | —CH(CH$_3$)CH$_2$— | —phenyl-NHCO— | —CH(CH$_3$)CH$_2$SO$_2C_{18}H_{37}$(n) |

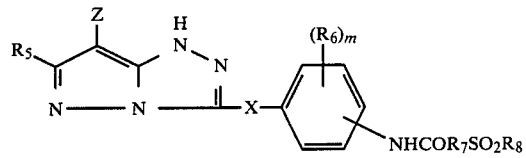

Formula (II)

| Coupler No. | $R_5$ | Z | X | ⟨⟩—NHCO— | $-R_7SO_2R_8$ |
|---|---|---|---|---|---|
| M-57 | $CH_3-$ | $Cl-$ | $-\underset{C_2H_5}{CH}-$ | ⟨⟩—NHCO— | $-CHCH_2SO_2-$⟨⟩$-OC_{12}H_{25}$ (n), with $CH_3$ on the CH |

The magenta couplers according to the present invention which are represented by formula (I) may be readily synthesized by any of the known techniques. The synthesis of one magenta coupler of formula (I) which may be used in the present invention is shown below.

Synthesis 1: Coupler M-1

To 150 ml of pyridine, 6-methyl-3-[3-(p-aminophenyl)propyl]-1H-pyrazole(3,2-c)-s-triazole (30 g) was added. At room temperature, dodecyl oxyphenylenesulfonylchloride (42.4 g) was added in small portions to the solution under agitation. Following 2-hr agitation, the reaction mixture was poured into ice water and extracted with ethyl acetate. The extract was washed with saturated aqueous sodium chloride twice and the ethyl acetate solution was dried over sodium sulfate. Then, ethyl acetate was distilled off. The resulting solid was subjected to chromatography on silica gel using ethyl acetate/hexane (1:1) as a solvent. By recrystallization from acetonitrile, a white crystal was obtained in a yield of 53.8 g.

Part (53.8 g) of the white crystal was dissolved in methyl chloride (500 ml), and under agitation at room temperature, N-chlorosuccinimide (12.4 g) was added in small portions to the solution. Following 1-hr agitation, the reaction mixture was washed with saturated aqueous sodium chloride twice, and the methylene chloride solution was dried over sodium sulfate. Then, methylene chloride was distilled off to give a solid product, which was recrystallized from acetonitrile to yield 32.1 g of the title coupler M-1, m.p. 97°–100° C. The structure of the coupler was determined by NMR and FD-mass analyses.

The magenta couplers according to the present invention that are represented by formula (II) may also be synthesized by various methods. A common route of synthesis is depicted below.

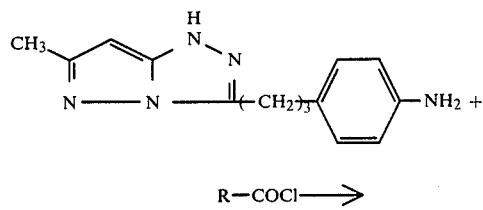

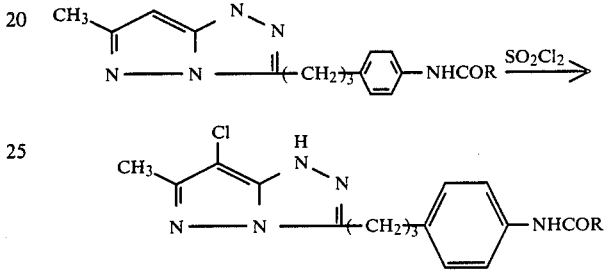

The synthesis of two magenta couplers of formula (II) is shown below.

Synthesis 2: Coupler 31

To a solution of anhydrous sodium acetate (4.5 g) in acetic acid (150 cc), 6-methyl-3-[3-(p-aminophenyl)-propyl]-1H-pyrazole (3,2-c)-s-triazole (12.7 g) was added at room temperature, and under agitation, α-benzylsulfonyltetradecanoyl chloride (22.1 g) was added in small portions. Following 5-hr agitation, the reaction mixture was poured into water. An oily product formed. It was extracted with ethyl acetate and washed with water. The oily layer was separated and dried with anhydrous magnesium sulfate. After distilling off the solvent under vacuum, the residue was purified by column chromatography on silica gel, and crystallized with ethyl acetate and n-hexane to give a white powder (16.7 g).

Part (15.0 g) of the white powder was uniformly dissolved in chloroform (150 cc), and under cooling with iced water at 10° C.±5° C., a solution of sulfuryl chloride (3.6 g) in chroroform (50 cc) was slowly added dropwise over a period of 1 hr. Following reaction for another one hour at the same temperature, the reaction mixture was poured into water for washing and separating the chloroform layer. It was dried with anhydrous magnesium sulfate and the solvent was distilled off under vacuum. The residue was purified by column chromatography on silica gel and recrystallized with acetonitrile.

A white powder (5.5 g) having mp. 75°–79° C. formed, and its structure was determined by NMR and MASS analyses.

Synthesis 3: Coupler 37

To a solution of anhydrous sodium acetate (4.5 g) in acetic acid (150 cc), 6-methyl-3-[3-(p-aminophenyl)-propyl]-1H-pyrazole (3,2-c)-s-triazole (12.7 g) was added at room temperature, and under agitation, α-(P- dodecyloxyphenylsulfonyl)butanoyl chloride (23.6 g) was added in small portions. Following 5-hr agitation, the reaction mixture was poured into water. An oily product formed. It was extracted with ethyl acetate and washed with water. The oily layer was separated and dried with anhydrous magnesium sulfate. After distilling off the solvent under vacuum, the residue was purified by column chromatography on silica gel to give an oil (20.0 g).

Part (15.0 g) of the oil was dissolved in chloroform (150 cc), and under cooling with iced water at 10° C.±3° C., a solution of sulfuryl chloride (3.4 g) in chloroform (50 cc) was added dropwise over a period of one hour. Following reaction for another one hour at the same temperature, water was added for washing and separating the chloroform layer. It was dried with anhydrous magnesium sulfate and the solvent was distilled off under vacuum. The residue was subjected to column chromatography on silica gel to obtain a colorless caramel-like product (4.4 g). Its structure was determined by NMR and MASS analyses.

Photographic emulsions prepared by using the magenta couplers according to the present invention may also contain other dye forming couplers. Preferred couplers for use in the present invention include those which are nondiffusible due to the presence of hydrophobic "ballast" groups in the molecule, those which produce dyes in such amounts that they will not leak from the photographic emulsion, and those which produce only slightly mobile dyes. The photographic emulsion may also contain couplers such as DIR couplers, blocked couplers and colored couplers (all these couplers exhibit various effects upon development).

Known open-chain ketomethylene compounds may be used as yellow dye forming couplers. Among these, pivaloyl acetanilide and benzoyl acetanilide couplers are useful. Illustrative yellow dye forming couplers are shown in U.S. Pat. No. 2,875,057, British Pat. No. 1,077,874, U.S. Pat. No. 3,408,194, Japanese Patent Public Disclosure Nos. 123342/1975, 87650/1975, and 133329/1979, Japanese Patent Publication No. 19031/1971, Japanese Patent Public Disclosure Nos. 66835/1973, 94432/1973, 28834/1975, 99433/1979, 70841/1980, and 74249/1981, Japanese Patent Publication No. 19956/1970, as well as Japanese Patent Public Disclosure Nos. 102636/1976 and 87041/1981.

Suitable cyan dye forming couplers are phenolic and naphtholic compounds. Illustrative cyan dye forming couplers are shown in U.S. Pat. Nos. 2,369,929, 2,474,293, 2,772,162 and 2,895,826, British Pat. No. 1,038,331, Japanese Patent Publication No. 36894/1973, Japanese Patent Public Disclosure No. 21139/1972, U.S. Pat. No. 3,737,316, Japanese Patent Public Disclosure No. 74844/1973, U.S. Pat. Nos. 3,880,661, 4,124,396, and 4,333,999, Japanese Patent Public Disclosure Nos. 21094/1980, 112038/1975, 117422/1975, 18315/1977, 115230/1979, 163537/1980, 136650/1982, 155538/1982, 204545/1982, 32071/1980, 108662/1980, 1938/1981, 27147/1981, 80045/1981 and 104333/1981.

The magenta dye forming couplers defined above according to the present invention may be used either alone or in combination with themselves. If desired, they may be used in combination with known magenta dye forming couplers such as pyrazolone, indazolone, cyanoacetyl, pyrazolinobenzimidazole and pyrazolotriazole compounds. However, it should be emphasized that at least one of the magenta dye forming couplers used in the present invention must be the compound of formula (I) or (II).

The magenta coupler according to the present invention is used in a manner similar to that used with conventional magenta dye forming couplers. Typically, the magenta coupler of the present invention is incorporated in a silver halide emulsion, which is then applied to a base to form a silver halide color photographic material. The silver halide photographic material may be monochromatic or multi-colored. In the latter case, the magenta coupler of the present invention is usually incorporated in a green-sensitive emulsion, but if desired, the coupler may be incorporated in a non-sensitive emulsion or an emulsion which is sensitive to the primary color regions in the spectrum other than green.

Each of the units that are used in the silver halide color photographic material of the present inveniton for providing dye images is made of one or more emulsion layers having sensitivity to specified ranges in the spectrum.

The layers necessary for making the silver halide color photographic material including the image forming layers may be arranged in various orders known in the art. A typical multi-colored silver halide photographic material consists of a cyan dye image forming unit comprising at least one red-sensitive silver halide emulsion layer containing at least one cyan dye forming coupler, a magenta dye image forming unit comprising at least one green-sensitive silver halide emulsion layer containing at least one magenta dye forming coupler as defined in the present invention, and a yellow dye image forming unit comprising at least one blue-sensitive silver halide emulsion layer containing at least one yellow dye forming coupler, with these three image forming units carried successively on a support.

The photographic material according to the present invention may contain additional layers such as a filter layer, an intermediate layer, a protective layer and a subbing layer.

The magenta dye forming coupler according to the present invention may be incorporated in a silver halide photographic material by any of the known methods. For example, the magenta dye forming coupler according to the present invention is dissolved in a mixture of a known high-boiling solvent and a low-boiling solvent such as butyl acetate or butyl propionate; the solution is then mixed with an aqueous solution of gelatin containing a surfactant; the mixture is emulsified with a high-speed rotary mixer, colloid mill or an ultrasonic disperser, and the resulting emulsion is added to a separately prepared silver halide, thereby forming a desired silver halide emulsion for use in the present invention.

Typical known high-boiling solvents include phthalate esters (e.g. dibutyl phthalate and dioctyl phthalate), phosphate esters (e.g. tricresyl phosphate and trioctyl phosphate) and N-substituted acid amides (e.g. N,N-diethyllaurylamide).

The silver halide color photographic material of the present invention preferably uses a non-color forming and non-diffusible phenolic compound (hereunder referred to as the phenolic compound of the present invention). If the phenolic compound of the present invention is used, it is preferably incorporated in a silver halide emulsion layer that contains the magenta dye forming coupler according to the present invention.

The phenolic compound of the present invention may be selected from among any of the non-color forming compounds which are preferably non-diffusible. For example, known phenolic high-boiling organic solvents commonly used for preparing coupler dispersions may be used.

Preferred phenolic compounds of the present invention are those which have melting points not higher than 50° C. and which are solid at normal temperature (25° C.), or those which are liquid at normal temperature and which have boiling points higher than 200° C. at normal pressure (one atmosphere).

The phenolic compound of the present invention preferably has a group for imparting the non-diffusible nature.

Preferred phenolic compounds of the present invention are represented by the following formula (III):

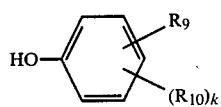

wherein $R_9$ and $R_{10}$ are each a halogen atom, an alkyl group, a cycloalkyl group or an alkoxy group; k is an integer of 0 to 4, provided that when k is 2 or more, $R_{10}$ may be the same or different groups, and $R_9$ and $R_{10}$ may be fused together to form a 5- or 6-membered ring.

In formula (III), the halogen atom represented by $R_9$ or $R_{10}$ is preferably a chlorine atom; the alkyl group represented by $R_9$ or $R_{10}$ preferably has 1 to 20 carbon atoms, and suitable examples are substituted or unsubstituted straight- or branched-chain alkyl groups such as methyl, ethyl, phenetyl, 2-(p-hydroxyphenyl)propane-2-yl, 1-(p-hydroxyphenyl)butane-1-yl, iso-propyl, butyl, tert-butyl, amyl, sec-amyl, tert-amyl, hexyl, octyl, tert-octyl, decyl, dodecyl, and 8-hexadecenyl; the cycloalkyl group represented by $R_9$ or $R_{10}$ is preferably a cyclohexyl group; the alkoxy group represented by $R_9$ or $R_{10}$ preferably has 1 to 20 carbon atoms and suitable examples include methoxy, ethoxy, iso-propoxy, tert-butoxy, phenetyloxy, ethoxyethyloxy, octyloxy, nonyloxy, decyloxy, dodecyloxy and octadecyloxy groups.

In formula (III), k represents an integer of 0 to 4, preferably 0 to 3, and the number 0 or 1 is particularly preferred.

In formula (III), the alkyl group, cycloalkyl group or alkoxy group represented by $R_9$ or $R_{10}$ is preferably a group which is capable of rendering the phenol non-diffusible either alone or in combination with $R_{10}$ or $R_9$. The total number of the carbon atoms in $R_9$ and $R_{10}$ is preferably 6 to 30, with the range of 8 to 25 being particularly preferred.

As mentioned above, $R_9$ and $R_{10}$ in formula (III) may be fused together to form a 5- or 6-membered ring. Preferred rings include hydroxyindane (e.g. 2,2-dimethyl-4-tert-octyl-6-indanole), hydroxychroman (e.g. 2,2-dimethyl-4-tert-butyl-7-octyl-6-chromanol), dihydroxyspirochroman (e.g. spiro[7-tert-butyl-6-hydroxy-4,4-dimethyl-2,2-chroman]), hydroxycoumaran (e.g. 2-butyl-6-octyl-5-coumaranol), hydroxybenzodioxane (e.g. 2,3-dimethyl-6-tert-octyl-7-hydroxybenzoxane), and hydroxybenzodioxorane (e.g. 2,2-dimethyl-4-dodecyl-5-hydroxybenzodioxorane). The hydroxychroman ring is particularly preferred.

Typical examples of the phenolic compound of the present invention are listed below, but it should be understood that the scope of the present invention is by no means limited to these examples.

Phenolic compounds:

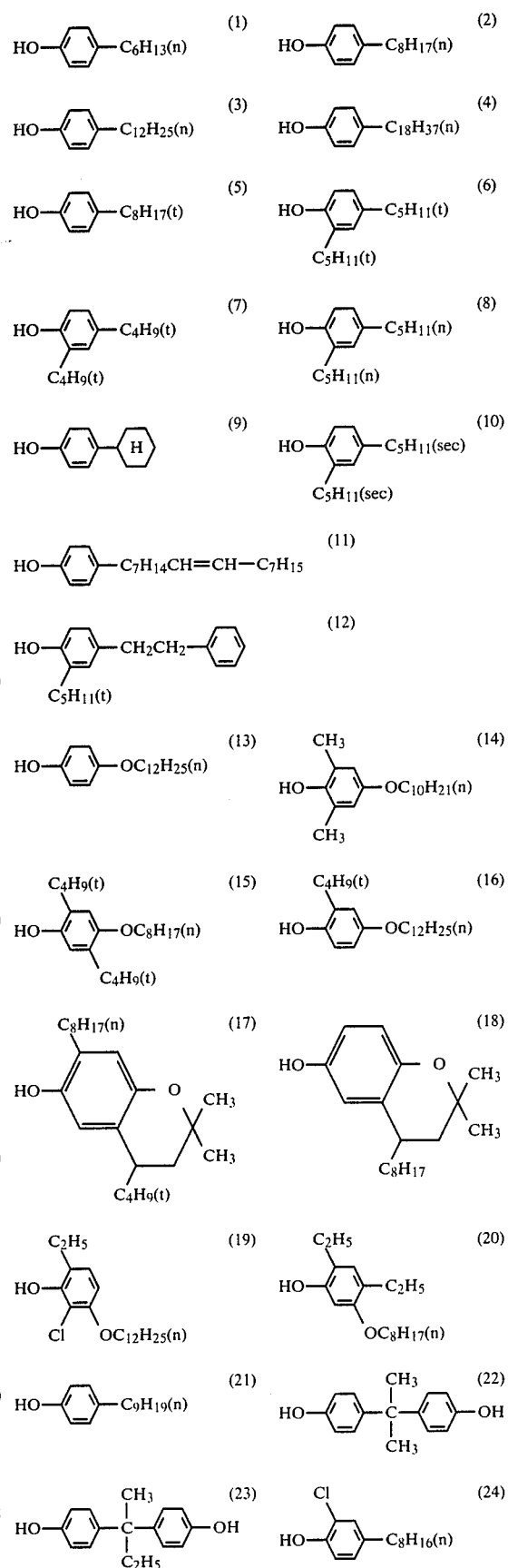

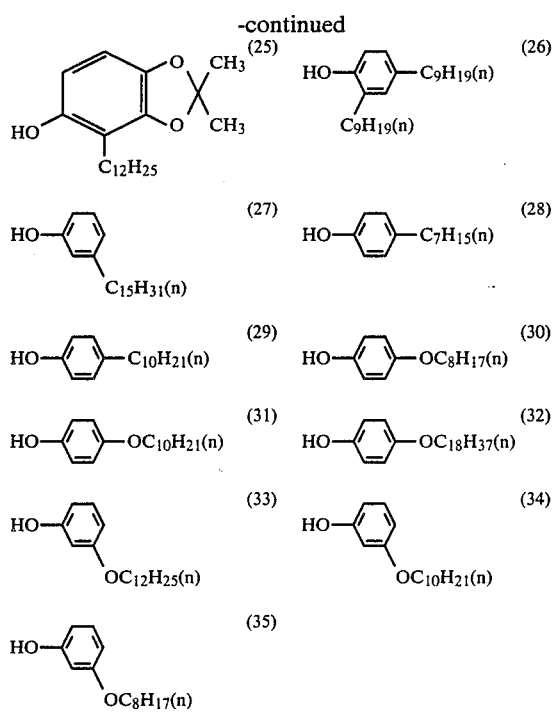

The phenolic compound of the present invention can be readily synthesized by any of the known methods, such as the one shown in U.S. Pat. No. 2,835,579. Many of the phenolic compounds of the present invention are commercially available, and compounds (3), (5), (6) and (21) listed above are examples of this group.

The magenta dye forming coupler and the phenolic compound of the present invention may be incorporated in a silver halide photographic material by any of the known methods. For example, the magenta dye forming coupler and phenolic compound of the present invention are dissolved in a mixture of a known high-boiling solvent (as illustrated above in connection with the description of the magenta dye forming coupler) and a low-boiling solvent (as already defined above); the solution is then mixed with an aqueous solution of gelatin containing a surfactant; the mixture is emulsified with a high-speed rotary mixer, colloid mill or an ultrasonic disperser, and the resulting emulsion is added to a separately prepared silver halide, thereby forming a desired silver halide emulsion for use in the present invention.

Some of the phenolic compounds of the present invention may be used as high-boiling solvents pre se, and compounds (2), (3), (6), (10) and (21) are examples of this group. If these compounds are used, other high-boiling solvents such as phthalate esters need not be used. The phenolic compound of the present invention may be dispersed separately from the magenta coupler of the present invention, and the two are individually added to the same silver halide emulsion. Preferably, the two are dissolved and added in the silver halide emulsion simultaneously.

For incorporation in the silver halide emulsion, the magenta coupler according to the present invention is used in an amount which generally ranges from about 0.01 to 2 mols, preferably from 0.03 to 0.5 mol, per mol of silver halide.

The greater the amount of the phenolic compound of the present invention that is used in comparison with the magenta coupler of the present invention, the more favorable it is to the objects of the present invention. Stated more specifically, the phenolic compound of the present invention is used in an amount of 0.1 to 10 g, preferably 0.25 to 3 g, per gram of the magenta coupler of the present invention.

The silver halide used in the silver halide emulsion according to the present invention is selected from among any of those which are used in conventional silver halide emulsions, such as silver bromide, silver chloride, silver iodobromide, silver chlorobromide and silver chloroiodobromide.

The silver halide emulsions making up the silver halide emulsion layers according to the present invention may be prepared by any of the common techniques. A typical example is shown in Japanese Patent Publication No. 7772/1971 and concerns the production of a "conversion emulsion": an emulsion of silver salt particles at least part of which has a higher solubility than silver bromide is first prepared, and then, at least part of these grains is converted to silver bromide or silver iodobromide. Alternatively, the method for preparing a Lippmann emulsion composed of fine silver halide grains having an average size of 0.1 μm or less may be employed.

The silver halide emulsions according to the present invention may be chemically sensitized by a sulfur sensitizer (e.g. arylthiocarbamide, thiourea or cystine), an active or inactive selenium sensitizer, a reduction sensitizer (e.g. stannous salt or polyamine), a noble metal sensitizer such as a gold sensitizer (e.g. potassium aurithiocyanate, potassium chloroaurate or 2-aurosulfobenzothiazole methyl chloride) or a water-soluble salt of ruthenium, rhodium or iridium (e.g. ammonium chloropalladate, potassium chloroplatinate or sodium chloropalladite). These chemical sensitizers may be used either alone or in combination.

The silver halide emulsions used in the present invention may contain various known photographic additives, such as those shown in Research Disclosure, December 1978, No. 17643.

The silver halide used in the present invention may be spectrally sensitized with a suitable sensitizing dye for the purpose of affording sensitivity to the necessary wavelength range. Various spectral sensitizers may be employed either alone or in combination. Those which are used with advantage in the present invention are cyanine dyes, merocyanine dyes or complex cyanine dyes of the types shown in U.S. Pat. Nos. 2,269,234, 2,270,378, 2,442,710, 2,454,520 and 2,776,280.

The support used in the present invention may be properly selected from among known materials depending upon the specific type of the photographic material used, and suitable support materials are plastic films, plastic-laminated paper, baryta paper, and synthetic paper. These supports are generally subbed to provide a stronger adhesion to a photographic emulsion layer.

The silver halide color photographic material of the present invention shown above is exposed and subjected to various methods of color development. A color developer preferably used in processing the photographic material of the present invention contains an aromatic primary amine color developing agent as the main component. Typical color developing agents are p-phenylenediamine compounds, such as diethyl-p-phenylenediamine hydrochloride, monomethyl-p-phenylenediamine hydrochloride, dimethyl-p- phenylenediamine-hydrochloride, 2-amino-5-diethylaminotoluene hydrochloride, 2-amino-5-(N-ethyl-N-dodecylamino)-toluene, 2-amino-5-(N-ethyl-N-$\beta$-methanesulfonamidoethyl)aminotoluene sulfate, 4-(N-ethyl-N-$\beta$-methanesulfonamidoethylamino)aniline, 4-(N-ethyl-N-$\beta$-hydroxyethylamino)aniline, and 2-amino-5-(N-ethyl-$\beta$-methoxyethyl)aminotoluene. These color developing agents may be used either alone or in combination with themselves. They may also be used with black-and-white developing agents such as hydroquinone. The color developing solutions used in the present invention generally contain an alkali agent such as sodium hydroxide, ammonium hydroxide, sodium carbonate or sodium sulfite, as well as other additives such as an alkali metal halide (e.g. potassium bromide) and a development regulator (e.g. hydrazine acid).

The silver halide color photographic material of the present invention may contain the color developing agent in a hydrophilic colloidal layer in the form of its precursor. A precursor of the color developing agent is a compound that is capable of producing the developing agent under alkaline conditions. Illustrative precursors are Schiff base precursors with aromatic aldehyde derivatives, polyvalent metallic ion complex precursors, phthalimide derivative precursors, phosphamide derivative precursors, sugar-amine reaction product precursors, and urethane precursors. Illustrative precursors for the aromatic primary color developing agent are shown in U.S. Pat. Nos. 3,342,599, 2,507,114, 2,695,234, 3,719,492, British Pat. No. 803,783, Japanese Patent Public Disclosure Nos. 135628/1978, 79035/1979, Research Disclosure Nos. 15,159, 12,146 and 13,924.

The aromatic primary amine color developing agents or their precursors shown above must be present in amounts sufficient to provide the desired color as a result of color development. The necessary amount varies significantly depending upon the type of the photographic material to be processed, and generally, it ranges from 0.1 mol to 5 mols, preferably from 0.5 mol to 3 mols, per mol of light-sensitive silver halide. The color developing agents or their precursors may be used either alone or in combination. These compounds may be incorporated in the photographic material either by dissolving them in a suitable solvent such as water, methanol, ethanol or acetone, or by using an emulsion in a high-boiling solvent such as dibutyl phthalate, dioctyl phthalate or tricresyl phosphate. If desired, the compounds may be impregnated in a latex polymer as shown in Research Disclosure No. 14850.

After color development, the silver halide color photographic material of the present invention is bleached, fixed and washed with water. The steps of bleaching and fixing may be performed simultaneously as a bleach-fixing step. While many compounds may be used as bleaching agents, compounds of polyvalent metals such as iron(III), cobalt(III) and tin(II) are preferably used. Particularly preferred compounds are complex salts of these polyvalent metallic cations and organic acids such as aminopolycarboxylic acids (e.g. ethylenediaminetetraacetic acid, nitrilotriacetic acid, and N-hydroxyethylenediaminediacetic acid), or organic acids (e.g. malonic acid, tartatic acid, malic acid, diglycolic acid and dithioglycolic acid). Alternatively, ferricyanates and bichromates may be used. These bleaching compounds may be used either alone or in combination.

The present invention is hereunder described in greater detail by reference to working examples, to which the possible embodiments of the present invention are by no means limited.

EXAMPLE 1

The magenta couplers shown in Table 1 (three of which were according to the present invention, and the other four were comparative couplers) were used. A tenth of a mole of each coupler per mol of silver was dissolved in an equal amount, by weight, of tricresyl phosphate, and three times the weight of the coupler of ethyl acetate. The mixture was heated at 60° C. to obtain a complete solution. The solution was mixed with 1200 ml of a 5% aqueous gelatin solution containing 120 ml of a 5% aqueous solution of Alkanol B (alkyl naphthalenesulfonate, a product of E. I. du Pont de Nemours & Co.), and an emulsion was prepared from the mixture by treatment with an ultrasonic disperser. The dispersion was mixed with 4 kg of a green-sensitive silver iodobromide emulsion (containing 6 mol of silver iodide) in the presence of 120 ml of a hardener, or 2% solution of 1,2-bis(vinylsulfonyl)ethane in water/methanol (1:1). The mixture was applied to a subbed transparent polyester base and the web was dried. By this procedure, samples 1 to 6 of silver halide photographic material were prepared. In all samples, the silver deposit was 20 mg/100 cm$^2$.

The samples thus prepared were exposed to light through a wedge by the conventional method and processed according to the following scheme. The results are shown in Table 1.

| Processing (38° C.) | Time |
|---|---|
| Color development | 3 min 15 sec |
| Bleaching | 1 min 30 sec |
| Washing | 3 min 15 sec |
| Fixing | 6 min 30 sec |
| Washing | 3 min 15 sec |
| Stabilizing | 1 min 30 sec |

The solutions used in the respective processing steps had the following formulations.

| Components | Amount (g) |
|---|---|
| Color developer | |
| 4-Amino-3-methyl-N—ethyl-N—($\beta$-hydroxyethyl)-aniline sulfate | 4.75 |
| Anhydrous sodium sulfite | 4.25 |
| Hydroxylamine hemisulfate | 2.0 |
| Anhydrous potassium carbonate | 37.5 |
| Sodium bromide | 1.3 |
| Nitrolotriacetic acid trisodium salt (monohydrate) | 2.1 |
| Potassium hydroxide | 1.0 |
| Water to make | 1,000 ml |
| pH adjusted to 10.0 with KOH | |
| Bleaching solution | |
| Ethylenediaminetetraacetic acid iron ammonium salt | 100.0 g |
| Ethylenediaminetetraacetic acid diammonium salt | 10.0 g |
| Ammonium bromide | 150.0 g |
| Glacial acetic acid | 10.0 ml |
| Water to make | 1,000 ml |
| pH adjusted to 6.0 with ammonia water | |
| Fixing solution | |
| Ammonium thiosulfate (50% aq. sol.) | 162 ml |
| Anhydrous sodium sulfite | 12.4 g |
| Water to make | 1,000 ml |
| pH adjusted to 6.5 with acetic acid | |
| Stabilizing bath | |
| Formalin (37% aq. sol.) | 5.0 ml |

-continued

| Components | Amount (g) |
|---|---|
| Konidax (product of Konishiroku Photo Industry Co., Ltd.) | 7.5 ml |
| Water to make | 1,000 ml |

TABLE 1

| Sample No. | Coupler | Specific sensitivity*[1] | Maximum density | Formalin resistance*[2] |
|---|---|---|---|---|
| 1 | Comparative coupler 1 | 100 | 1.25 | 35 |
| 2 | Comparative coupler 2 | 130 | 1.31 | 40 |
| 3 | Comparative coupler 3 | 125 | 1.35 | 37 |
| 4 | M - 2 | 150 | 2.51 | 63 |
| 5 | M - 4 | 132 | 1.30 | 49 |
| 6 | M - 7 | 138 | 1.53 | 48 |

*[1]The specific sensitivity is the reciprocal of exposure that gave a density equal to fog + 0.1. The data on specific sensitivity is based on relative values, with the value for comparative coupler 1 being taken as 100.
*[2]Before color development, each sample was held in a closed vessel (30° C., 62% R.H.) containing 6 cc of 0.9% formalin for 3 days. As a control, a sample that was not treated with formalin was developed. The formalin resistance was calculated by the following formula:

Formalin resistance = $\frac{\text{Color density of formalin-treated sample}}{\text{Color density of untreated sample}} \times 100(\%)$ Comparative coupler 1:

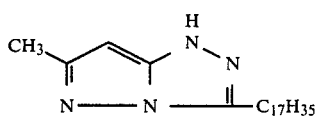

Comparative coupler 2:

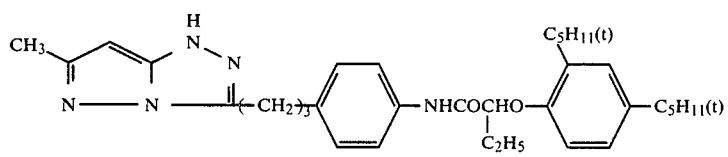

Comparative coupler 3:

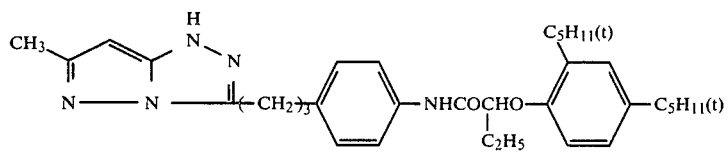

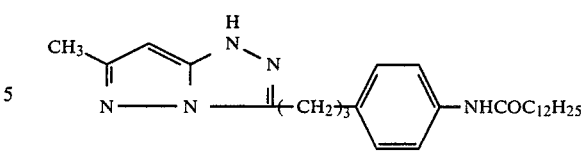

Sample Nos. 4 to 6 using the couplers according to the present invention had higher color sensitivities and maximum densities, as well as better formalin resistance than sample Nos. 1 to 3 using the comparative couplers.

EXAMPLE 2

Silver halide color photographic samples were prepared using three magenta couplers according to the present invention and three comparative couplers. The six samples were processed photographically as in Example 1, and the results are shown in Table 2.

TABLE 2

| Sample No. | Couple | Specific sensitivity*[1] | Maximum density | Formalin resistance*[2] |
|---|---|---|---|---|
| 7 | Comparative coupler 5 | 100 | 2.67 | 81 |
| 8 | Comparative coupler 4 | 130 | 3.38 | 95 |
| 9 | Comparative coupler 6 | 155 | 2.88 | 56 |
| 10 | M - 1 | 160 | 2.92 | 89 |
| 11 | M - 5 | 203 | 3.21 | 87 |
| 12 | M - 13 | 187 | 3.11 | 91 |

Comparative coupler 4:

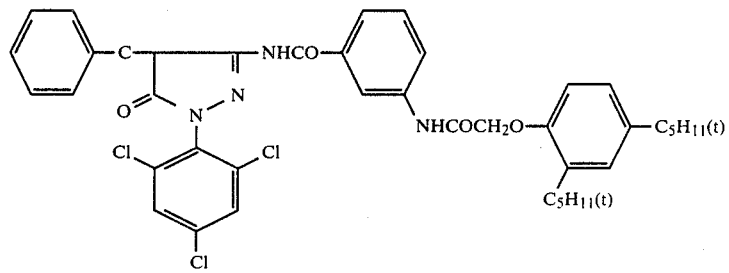

Comparative coupler 5 (as shown in Japanese Patent Public Disclosure No. 42045/1983):

Comparative coupler 6 (as shown in Japanese Patent Publication No. 16058/1974):

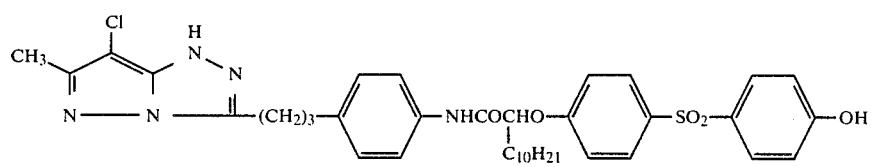

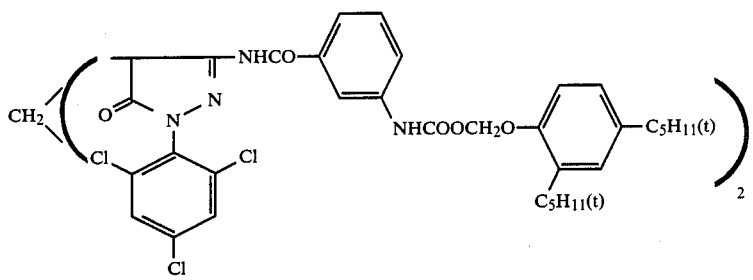

Sample Nos. 10 to 12 using the magenta couplers according to the present invention had higher color sensitivities and maximum densities, as well as better formalin resistance than sample Nos. 7 to 9 using the comparative couplers.

As will be apparent from Examples 1 and 2, the magenta couplers according to the present invention have high sensitivity and exhibit high color density, and furthermore, they have good keeping quality in that they can be stored in the presence of formalin for an extended period. Therefore, a silver halide color photographic material having a stable color balance can be prepared by applying to a transparent support a blue-sensitive silver halide emulsion layer containing an open-chain active methylene yellow coupler, a green-sensitive silver halide emulsion layer containing the magenta coupler of the present invention, and a red-sensitive silver halide emulsion layer containing a phenolic or naphtholic cyan coupler, each emulsion layer containing suitable photographic additives and being applied by a conventional technique.

EXAMPLE 3

The magenta couplers shown in Table 3 (three of which were according to the present invention, and the other three were comparative couplers) were used. A tenth of a mole of each coupler per mol of silver was dissolved in an equal amount, by weight, of tricresyl phosphate, a suitable amount of the phenolic compound of the present invention, and three times the weight of the coupler of ethyl acetate. The mixture was heated at 60° C. to obtain a complete solution. The solution was mixed with 1200 ml of a 5% aqueous gelatin solution containing 120 ml of a 5% aqueous solution of Alkanol B (alkylnaphthalenesulfonate, a product of E. I. du Pont de Nemours & Co.), and an emulsion was prepared from the mixture by treatment with an ultrasonic disperser. The dispersion was mixed with 4 kg of a green-sensitive silver iodobromide emulsion (containing 6 mol% of silver iodide) in the presence of 120 ml of a hardener, or 2% solution of 1,2-bis(vinylsulfonyl)ethane in water/methanol (1:1). The mixture was applied to a subbed transparent polyester base and the web was dried. By this procedure, sample Nos. 13 to 27 of silver halide photographic material were prepared. In all samples, the silver deposit was 20 mg/100 cm$^2$.

The samples thus prepared were exposed to light through a wedge by the conventional method and processed according to the scheme which was the same as used in Example 1. The processing solutions also had the same compositions as those used in Example 1. The results of Example 3 are shown in Table 3 below.

TABLE 3

| Sample No. | Coupler | HBS*[1] | Phenolic compound of the present invention No. | Amount*[2] | Specific sensitivity*[3] | Maximum density | Formalin resistance*[4] | Maximum spectral absorption (λ max)*[5] |
|---|---|---|---|---|---|---|---|---|
| 13 | Comparative coupler 4 | o | — | — | 130 | 3.38 | 95 | 554 |
| 14 | Comparative coupler 4 | — | 8 | 1.0 | 135 | 3.43 | 90 | 561 |
| 15 | Comparative coupler 6 | o | — | — | 155 | 2.88 | 56 | 551 |
| 16 | Comparative coupler 6 | — | 8 | 1.0 | 160 | 2.93 | 57 | 555 |
| 17 | Comparative coupler 5 | o | — | — | 100 | 2.67 | 81 | 552 |
| 18 | Comparative coupler 5 | — | 8 | 1.0 | 130 | 2.80 | 85 | 559 |
| 19 | M - 1 | — | 6 | 1.0 | 180 | 3.10 | 93 | 553 |
| 20 | " | o | 17 | 0.5 | 175 | 3.15 | 93 | 551 |
| 21 | " | — | 3 | 1.0 | 180 | 3.20 | 94 | 554 |
| 22 | M - 5 | — | 6 | 1.0 | 215 | 3.40 | 95 | 554 |
| 23 | " | — | 21 | 1.0 | 210 | 3.45 | 93 | 555 |
| 24 | " | o | 7 | 0.5 | 215 | 3.35 | 91 | 553 |
| 25 | M - 22 | o | 5 | 1.0 | 190 | 3.20 | 95 | 555 |
| 26 | " | — | 3 | 1.0 | 185 | 3.30 | 93 | 554 |
| 27 | " | o | 20 | 0.5 | 195 | 3.25 | 94 | 555 |

*[1] HBS indicates tricresyl phosphate. The symbol (—) means the non-use of HBS and (o) means its use.
*[2] The amount of the phenolic compound of the present invention used is indicated in terms of the relative value given by:
$$\frac{\text{Weight of phenolic compound}}{\text{Weight of coupler}}$$
*[3] Same as defined in Example 1.
*[4] Same as defined in Example 1.
*[5] The maximum spectral absorption was the wavelength in nm of the peak absorption of a color developed sample for a density of 1.0.

Comparative couplers 4, 5 and 6 were the same as those defined in Example 2.

As Table 3 shows, comparative coupler 4 was improved with respect to maximum color density and formalin resistance, but its sensitivity was not completely satisfactory, and the addition of the phenolic compound proved ineffective in providing an improved sensitivity. Comparative coupler 5 had some improvement in formalin resistance, but not in sensitivity or maximum color density. Comparative coupler 6 was somewhat improved in respect to sensitivity and maximum color density, but its formalin resistance was yet to be improved. Sample Nos. 19 to 27 using the combinations of the magenta couplers and phenolic compounds according to the present invention were improved in all respects, ie. sensitivity, maximum color density and formalin resistance.

EXAMPLE 4

The magenta couplers according to the present invention that are shown in Table 4 were used. A tenth of a mole of each coupler per mol of silver was dissolved in an equal amount, by weight of 2,4-di-tert-amylphenol of the same weight as each coupler, and three times the weight of the coupler of ethyl acetate.

The mixture was heated at 60° C. to obtain a complete solution. The solution was mixed with 1200 ml of a 5% aqueous gelatin solution containing 120 ml of a 5% aqueous solution of Alkanol B (alkyl naphthalenesulfonate, a product of E.I. Du Pont de Nemours & Co.), and an emulsion was prepared from the mixture by treatment with an ultrasonic disperser. The dispersion was mixed with 4 kg of a green-sensitive silver iodobromide emulsion (containing 6 mol of silver iodide) in the presence of 120 ml of a hardener, or 2% solution of 1,2-bis(vinylsulfonyl)ethane in water/methanol (1:1). The mixture was applied to a subbed transparent polyester base and the web was dried. In all samples, the silver deposit was 10 mg/100 cm$^2$.

The Samples Nos. 13, 15 and 17 used in Example 3 were also used for comparison. The samples thus prepared were exposed to light through a wedge by the conventional method and processed in the same manner as in Example 3. The results of Example 4 are shown in Table 4.

TABLE 4

| Sample No. | Coupler | HBS *(6) | Amount of silver (mg/100 cm$^2$) | Specific sensitivity | Maximum density |
|---|---|---|---|---|---|
| 28 | Comparative coupler 4 | TCP | 20 | 130 | 3.38 |
| 29 | Comparative coupler 5 | TCP | 20 | 100 | 2.67 |
| 30 | Comparative coupler 6 | TCP | 20 | 155 | 2.88 |
| 31 | M - 1 | DAP | 10 | 115 | 2.53 |
| 32 | M - 5 | DAP | 10 | 140 | 2.80 |
| 33 | M - 13 | DAP | 10 | 110 | 2.50 |
| 24 | M - 22 | DAP | 10 | 125 | 2.61 |
| 35 | M - 27 | DAP | 10 | 115 | 2.43 |

*(6): TCP represents tricresyl phosphate, and DAP 2,4-di-tert-amylphenol.

As Table 4 shows, the samples using the magenta couplers and phenolic compound according to the present invention required half the amount of the silver that was deposited in the comparative samples. Nevertheless, these samples exhibited sensitivity and maximum color density which were comparable to or higher than those achieved by the comparative couplers. This suggests the improved efficiency in the use of silver halide that is attained by using the megenta couplers of the present invention in combination with the phenolic compound of the present invention. As one can see, this combination provides a photographic material that fully satisfies the objects of the present invention by reducing the required amount of silver deposit, hence the thickness of the individual silver halide emulsion layers, and by providing improved sharpness to the underlying layers.

As will be readily understood from Examples 3 and 4, the magenta coupler of the present invention as combined with the phenolic compound of the present invention provides a high sensitivity and color density, as well as good keeping quality that is demonstrated by the consistent color forming ability in the presence of formalin. Therefore, a silver halide color photographic material having a stable color balance can be prepared by applying to a transparent support a blue-sensitive silver halide emulsion layer containing an open-chain active methylene yellow coupler, a green-sensitive silver halide emulsion layer containing the magenta coupler and phenolic compound of the present invention, and a red-sensitive silver halide emulsion layer containing a phenolic or naphtholic cyan coupler, each emulsion layer containing suitable photographic additives and being applied by a conventional technique.

EXAMPLE 5

The magenta couplers shown in Table 5 (nine of which were according to the present invention, and the other four were comparative couplers) were used. A tenth of a mole of each coupler per mol of silver was dissolved in an equal amount, by weight, of tricresyl phosphate, and three times the weight of the coupler of ethyl acetate. The mixture was heated at 60° C. to obtain a complete solution. The solution was mixed with 1200 ml of a 5% aqueous gelatin solution containing 120 ml of a 5% aqueous solution of Alkanol B (alkyl naphthalenesulfonate, a product of E.I. du Pont de Nemours & Co.), and an emulsion was prepared from the mixture by treatment with an ultrasonic disperser. The dispersion was mixed with 4 kg of a green-sensitive silver iodobromide emulsion (containing 6 mol of silver iodide) in the presence of 120 ml of a hardener, or 2% solution of 1,2-bis(vinylsulfonyl)ethane in water/methanol (1:1). The mixture was applied to a subbed transparent polyester base and the web was dried. By this procedure, samples 36 to 48 of silver halide photographic material were prepared. In all samples, the silver deposit was 20 mg/100 cm$^2$.

The samples thus prepared were exposed to light through a wedge by the conventional method and processed according to the following scheme. The results are shown in Table 5.

| Processing (35° C.) | Time |
|---|---|
| Color development | 4 min |
| Bleaching | 1 min 30 sec |
| Washing | 3 min 15 sec |
| Fixing | 6 min 30 sec |
| Washing | 3 min 15 sec |
| Stabilizing | 1 min 30 sec |

The solutions used in the respective processing steps were the same as those used in Example 1.

TABLE 5

| Sample No. | Coupler | Specific sensitivity*[1] | Maximum density | Formalin resistance*[2] |
|---|---|---|---|---|
| 36 | Comparative coupler 7 | 100 | 3.00 | 85 |
| 37 | Comparative coupler 2 | 30 | 1.25 | 33 |
| 38 | Comparative coupler 8 | 55 | 1.85 | 72 |
| 39 | Comparative coupler 9 | 70 | 2.50 | 81 |
| 40 | M - 32 | 110 | 3.15 | 86 |
| 41 | M - 33 | 130 | 3.35 | 90 |
| 42 | M - 35 | 135 | 3.30 | 88 |
| 43 | M - 37 | 145 | 3.40 | 90 |
| 44 | M - 40 | 140 | 3.50 | 92 |
| 45 | M - 44 | 125 | 3.45 | 94 |
| 46 | M - 46 | 145 | 3.55 | 91 |
| 47 | M - 48 | 140 | 3.60 | 93 |
| 48 | M - 50 | 135 | 3.35 | 90 |

*[1]: The specific sensitivity is the reciprocal of exposure that gave a density equal to fog + 0.1. The data on specific sensitivity is based on relative values, with the value for comparative coupler 7 taken as 100.
*[2]: Same as defined in Table 1.

Comparative coupler 7:

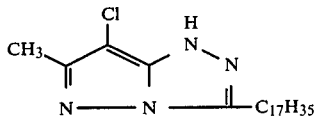

Comparative Coupler 2:
Same as comparative coupler 2 used in Example 1.
Comparative coupler 8:

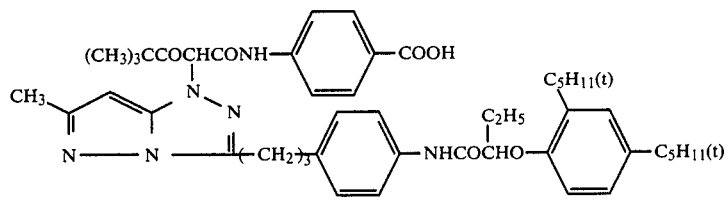

Comparative coupler 9:

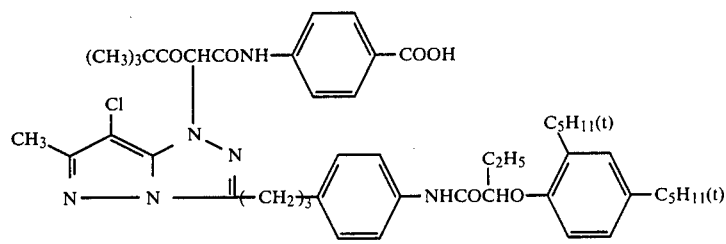

As Table 5 shows, comparative coupler 7 having a structure similar to that of the magenta coupler according to the present invention showed good results with respect to sensitivity, maximum density and formalin resistance. However, the results were not as good as what was intended by the present inventors. The structure of comparative coupler 2 was more similar to that of the magenta coupler of the present invention, and it had hydrogen at 7-position of the pyrazolotriazole nucleus. However, comparative coupler 2 had very low levels of specific sensitivity, maximum density and formalin. Comparative coupler 8, was a compound having the 1-position of comparative coupler 2 substituted by the active site of a compound having an active methylene group. This comparative coupler was characterized by improved formalin resistance. As Table 5 shows, comparative coupler 8 achieved some improvement in specific sensitivity and maximum density, but the degree of the improvement in these two respects was very low. Even the formalin resistance of this comparative coupler was not improved as greatly as it was desired to achieve. Comparative coupler 9 was a compound having the 7-position of comparative coupler 8 substituted by a chlorine atom. This comparative coupler had some improvement in respect of specific sensitivity, maximum density and formalin resistance, but the degree of the improvement was not completely satisfactory for the purposes of the present invention. Sample Nos. 40 to 48 using the magenta couplers of the present invention gave satisfactory results in respect of specific sensitivity, maximum density and formalin resistance.

Comparative couplers 2, 8 and 9 had a non-diffusible group which was the same as what was present in the magenta coupler of the present invention. The data in Table 5 shows that in order to ensure satisfactory results in all the respects of sensitivity, maximum density and formalin resistance, it is essential that the pyrazolotriazole nucleus be substituted at 1-position by a hydrogen atom and at 7-position by a group such as chlorine atom that is capable of coupling with the oxidized product of a color developing agent. These requirements were met by comparative coupler 7, but as Table 5 shows, the results with this comparative coupler were far from being satisfactory. Therefore, it will be understood that the advantages of the magenta coupler of the present invention are entirely unexpected.

What is claimed is:

1. A silver halide color photographic material having at least one silver halide emulsion layer on a support, said silver halide emulsion layer containing at least one magenta coupler of the following formula (I) or (II):

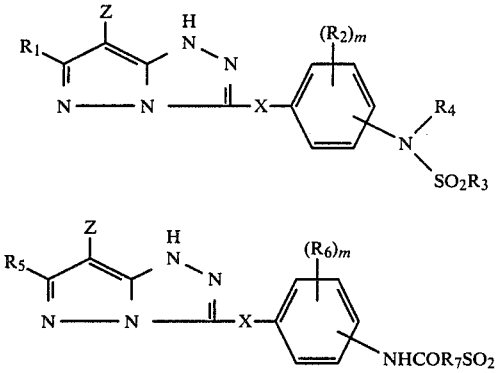

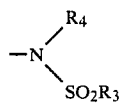

wherein R₁ and R₄ are each a hydrogen atom, an alkyl group or an aryl group; $R_2$ and $R_6$ are each a monovalent group; $R_3$ is an alkyl group, an aryl group or a heterocyclic group; $R_5$ is an alkyl group or an aryl group; $R_7$ is an alkylene group, an arylene group or a bivalent organic group having at least one alkylene bonded to at least one arylene; $R_8$ is an alkyl group, an alkenyl group, an aryl group or a heterocyclic group; X is a single bond or an alkylene group having 1 to 5 carbon atoms; Z is a hydrogen atom or a group that can be eliminated upon coupling reaction with the oxidized product of a color developing agent; and m is an integer of 0 to 4.

2. A silver halide color photographic material according to claim 1, wherein $R_1$ and $R_5$ is formulae (I) and (II) are each an alkyl group.

3. A silver halide color photographic material according to claim 2, wherein said alkyl group has 1 to 8 carbon atoms.

4. A silver halide color photographic material according to claim 1, wherein the monovalent group represented by $R_2$ and $R_6$ in formulas (I) and (II) is selected from the group consisting of a halogen atom, an alkoxy group, an alkyl group, a nitro group, and a cyano group.

5. A silver halide color photographic material according to claim 1, wherein Z in formulas (I) and (II) is selected from the group consisting of a halogen atom, an aryloxy group, an arylthio group, and a heterocyclic thio group.

6. A silver halide color photographic material according to claim 1, wherein the group in formula (I) is substituted on the phenyl group at paraposition.

7. A silver halide color photographic material according to claim 1, wherein the group —NHCOR₇SO₂R₈ in formula (II) is substituted on the phenyl group at paraposition.

8. A silver halide color photographic material according to claim 5, wherein Z is a halogen atom.

9. A silver halide color photographic material according to claim 1, wherein m is zero.

10. A silver halide color photographic material according to claim 1, wherein the alkyl group represented by $R_4$ has 1 to 38 carbon atoms.

11. A silver halide color photographic material according to claim 1, wherein the aryl group represented by $R_4$ is a phenyl group.

12. A silver halide color photographic material according to claim 1, wherein $R_7$ is an alkylene group having 1 to 20 carbon atoms.

13. A silver halide color photographic material according to claim 1, wherein $R_8$ is an alkyl group or an aryl group.

14. A silver halide color photographic material according to claim 13, wherein said alkyl group has 1 to 20 carbon atoms.

15. A silver halide color photographic material according to claim 13, wherein said aryl group is a phenyl group.

16. A silver halide color photographic material according to claim 1, wherein X in said formulas (I) and (II) is a group represented by $-(-CH_2-)_l$ (wherein l is an integer of 1 to 5).

17. A silver halide color photographic material according to claim 1, wherein X is a group selected from among methylene, 1,1-ethene, 1,2-ethylene, 1,3-propylene, 1,1-propylene, 1,2-propylene, 1,4-buthylene and 1,5-penthylene.

* * * * *